US00PP34356P2

(12) United States Plant Patent
Warren

(10) Patent No.: US PP34,356 P2
(45) Date of Patent: Jun. 21, 2022

(54) CRABAPPLE TREE NAMED 'JFS KW218MX'

(50) Latin Name: *Malus*
Varietal Denomination: JFS KW218MX

(71) Applicant: J. Frank Schmidt & Son Co., Boring, OR (US)

(72) Inventor: Keith S. Warren, Gresham, OR (US)

(73) Assignee: J. Frank Schmidt & Son Co., Boring, OR (US)

( * ) Notice: Subject to any disclaimer, the term of this patent is extended or adjusted under 35 U.S.C. 154(b) by 0 days.

(21) Appl. No.: 17/239,186

(22) Filed: Apr. 23, 2021

(51) Int. Cl.
*A01H 5/08* (2018.01)
*A01H 6/74* (2018.01)

(52) U.S. Cl.
USPC ..... Plt./173
CPC ..... *A01H 6/7418* (2018.05)

(58) Field of Classification Search
USPC ..... Plt./173
CPC ..... A01H 6/7418; A01H 5/08
See application file for complete search history.

*Primary Examiner* — Keith O. Robinson
(74) *Attorney, Agent, or Firm* — Klarquist Sparkman, LLP

(57) ABSTRACT

A variety of crabapple which combines a combination of a tight upright pyramidal growth habit, profuse single white flowers, dark green foliage that remains disease free through the summer. Small orange fruit and a strong resistance to the diseases fireblight, powdery mildew, and apple scab.

9 Drawing Sheets

Latin name of the genus of the plant claimed: *Malus*.
Variety denomination: 'JFS KW218MX'.

BACKGROUND OF THE INVENTION

In 1990, I began a program of ornamental crabapple cultivar development. As part of this program, I picked a large amount of open pollinated seed from various crabapples in the fall of 1992. I grew 918 resulting seedlings in seedbeds and then transplanted the best of the seedlings into nursery rows. In 1996, I discovered that one of these seedling trees was very unique in that it had an extremely short internode length, resulting in very dwarf habit. I named this tree 'KW-8MX' and allowed it to cross pollinate with other crabapple selections of mine and I collected its seed in 1999. I transplanted 'KW-8MX' into a long term evaluation block in 2000, but it was not attractive enough for commercial introduction. In 2004, among the many seedlings that I grew from the seed of 'KW-8MX', I discovered a unique tree with short internodes, a semi-dwarf growth habit, and much more attractive foliage and flowers than its seed parent. I named this new selection 'KW-83MX' and I picked its open pollinated seed in the fall of 2004. I transplanted 'KW-83MX' into a long term observation block with other superior crabapple selections of mine. Over time, observation convinced me that 'KW-83MX' was an extremely attractive selection with compact upright form, but still not quite up to the level of quality I desired for commercial introduction. The seed of 'KW-83MX' that I collected in 2004 resulted in a large number of seedling trees, and the best and most disease resistant of these were transplanted into a nursery row in 2007. In 2008, 2009, and 2010 I evaluated these open pollinated seedlings of 'KW-83MX' and discarded all but the very finest, which were transplanted on wider spacing in March of 2010. During 2011, one particular tree showed outstanding traits of heavy flowering, dense branching, high quality disease resistant foliage, and attractive ovoid yellow-orange ornamental fruit. I determined that this combination of traits differed from all other seedlings from the same seed parent, was unique and superior, and I named this selection 'JFS KW218MX', which is the subject of the present application.

All of the above growing and selection process took place in a nursery in Boring, Oreg. Each crop in the selection process was inoculated repeatedly with apple scab fungus, and susceptible trees were discarded. Also, at each stage of the selection process, trees that were not outstanding in appearance were discarded, so that out of many hundreds of seedling trees grown, only a few were kept for transplanting to the next level of the selection process.

In March of 2012, I transplanted my new crabapple variety, 'JFS KW218MX' into a long term experimental block in the Boring, Oreg. nursery for continued testing and evaluation. In 2014, 2015, 2016, and 2017, I test propagated my new variety by chip budding onto *Malus* rootstock in small test plots of 10 to 20 trees in a nursery in Canby, Oreg. In 2014, the rootstock used was *Malus domestica*. In 2015, 2016, and 2017, the rootstock used was *Malus* rootstock P18 (Polish 18; unpatented). None of these propagated trees were sold. In 2016, five of the propagated trees were sent to Washington State University for further testing for disease resistance and other characteristics, with the agreement that no propagation or distribution would be allowed. A further 81 were sent in 2017 for continued testing and were destroyed once testing was complete. Otherwise, all test propagated trees have been destroyed, except for 23 trees which I retained under my control to create stock for future propagation. Testing showed that my new tree displayed strong resistance to the disease fireblight. Observation of the trees produced from this asexual propagation has shown that the characteristics of my new tree variety are firmly fixed and the asexually propagated trees have been identical to the original tree in every manner that has been observed.

BRIEF SUMMARY OF THE INVENTION

This new cultivar possesses a unique combination of characteristics that have proven firmly fixed in asexually propagated progeny and that comprise a combination of a dense, compact, upright pyramidal growth habit, a dense bloom of attractive white flowers, attractive green foliage, small, ovoid, yellow-orange fruit, and strong resistance to the diseases including powdery mildew, fireblight and apple scab.

BRIEF DESCRIPTION OF THE DRAWINGS

The colors of an illustration of this type may vary with lighting conditions and, therefore, color characteristics of this new variety should be determined with reference to the observations described herein, rather than from these illustrations alone.

DETAILED BOTANICAL DESCRIPTION

Figure 1:
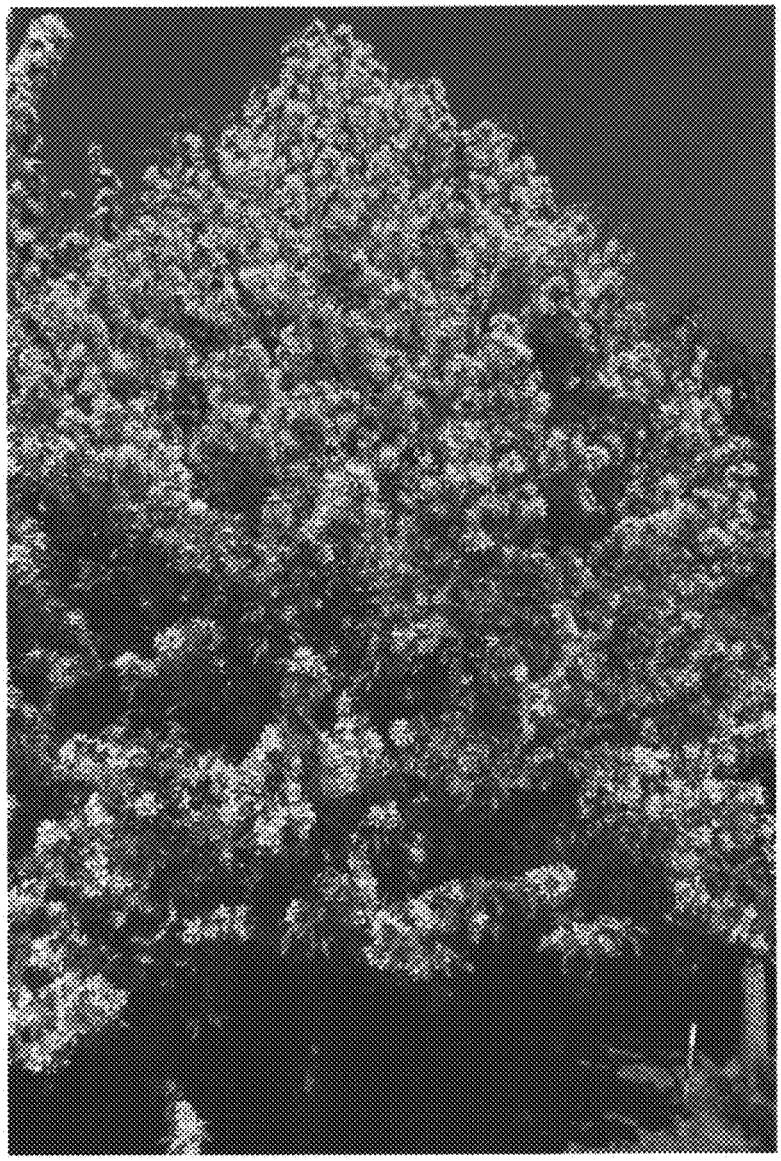
FIG. 1: Shows the original tree in flower at 10 years of age with foliage
Figure 2:
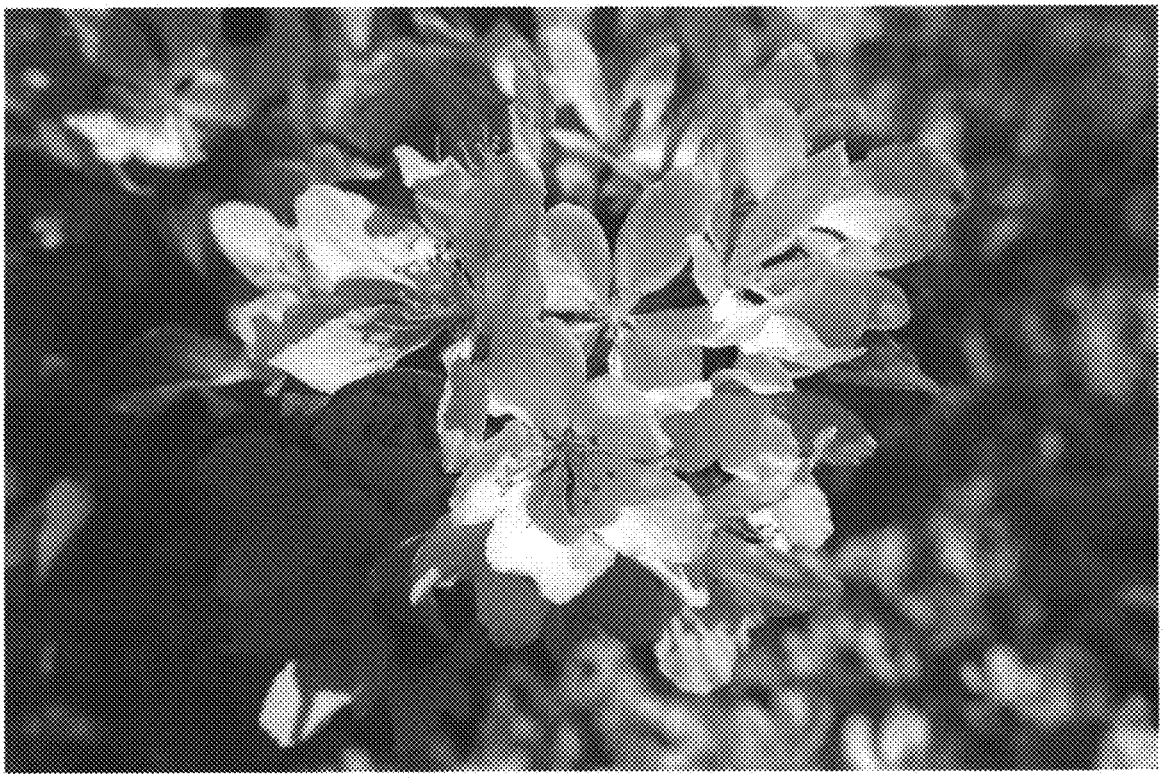
FIG. 2: Shows a close-up of the flowers on the original tree.
Figure 3:
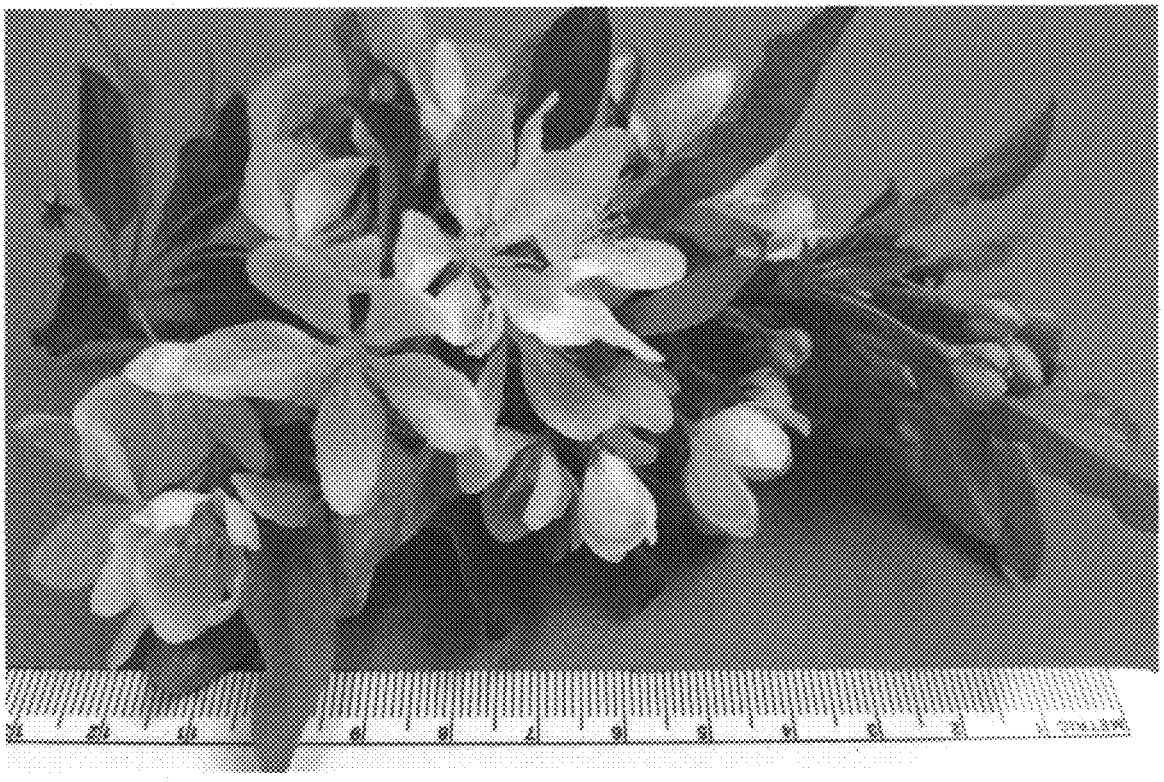
FIG. 3: Shows a close up of a few flowers & foliage on a display board with a scale.
Figure 4:
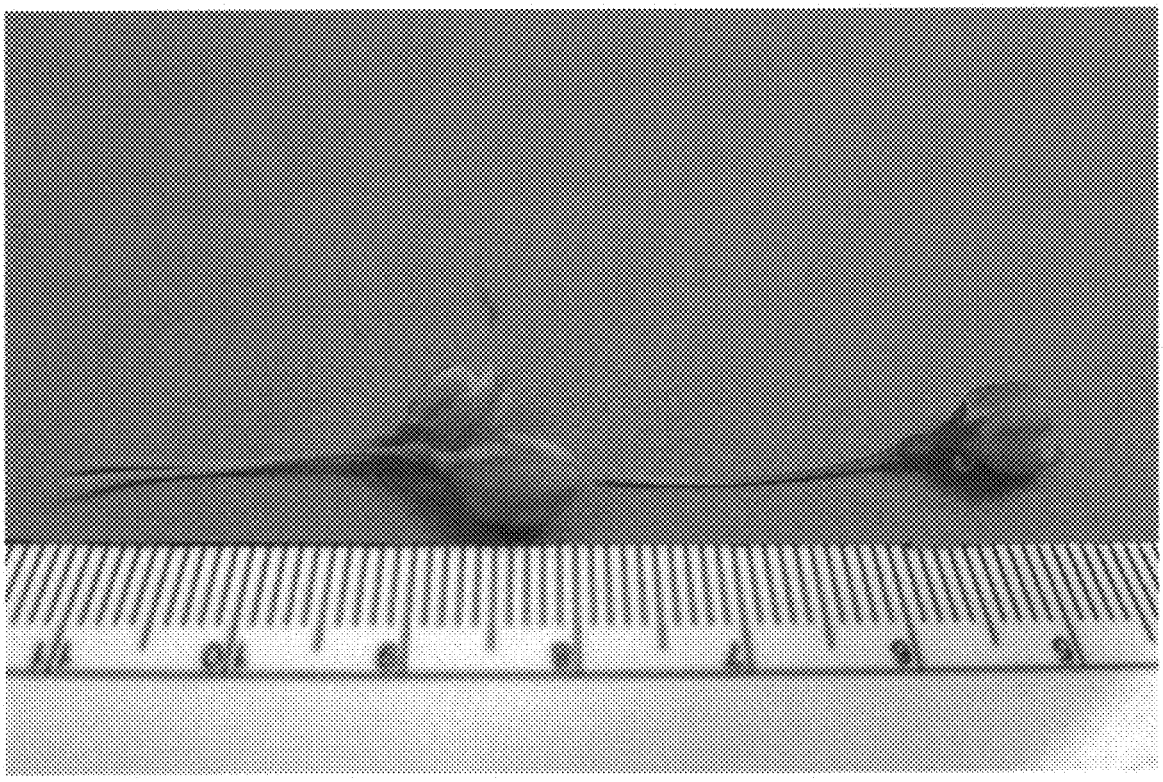
FIG. 4: Shows flower buds on a display board with a scale.
Figure 5:
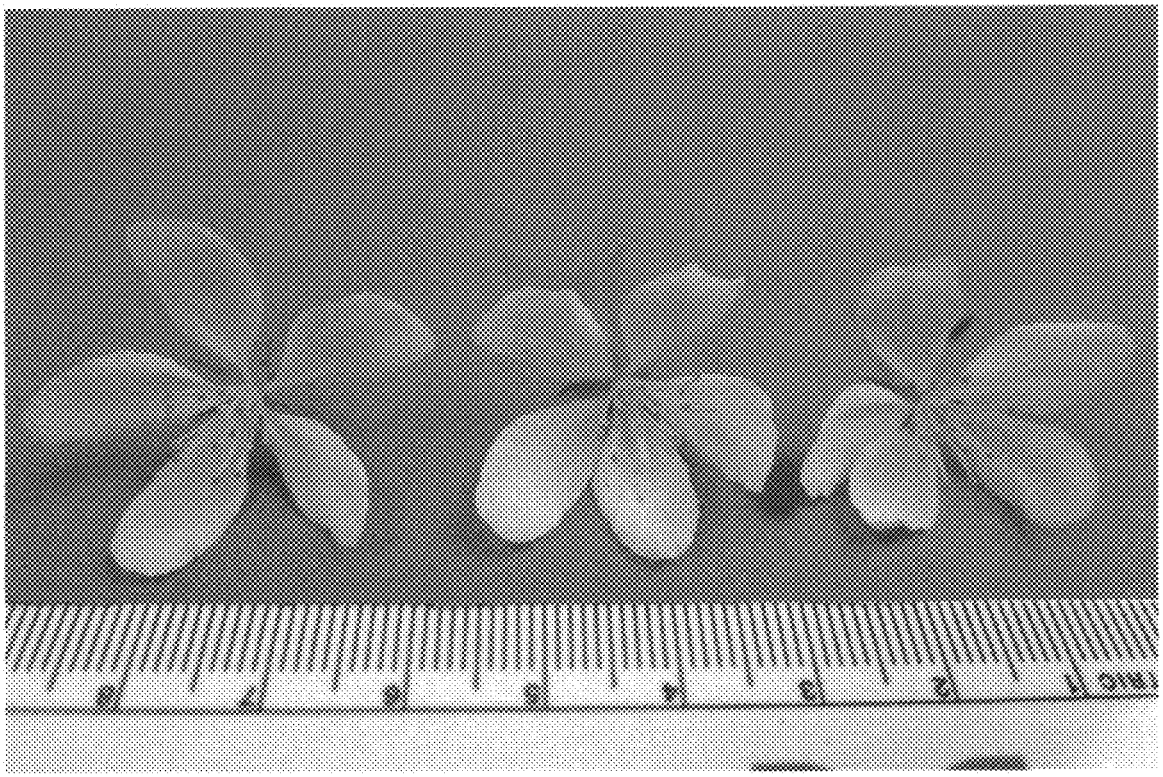
FIG. 5: Shows three flowers on a display board with scale
Figure 6:
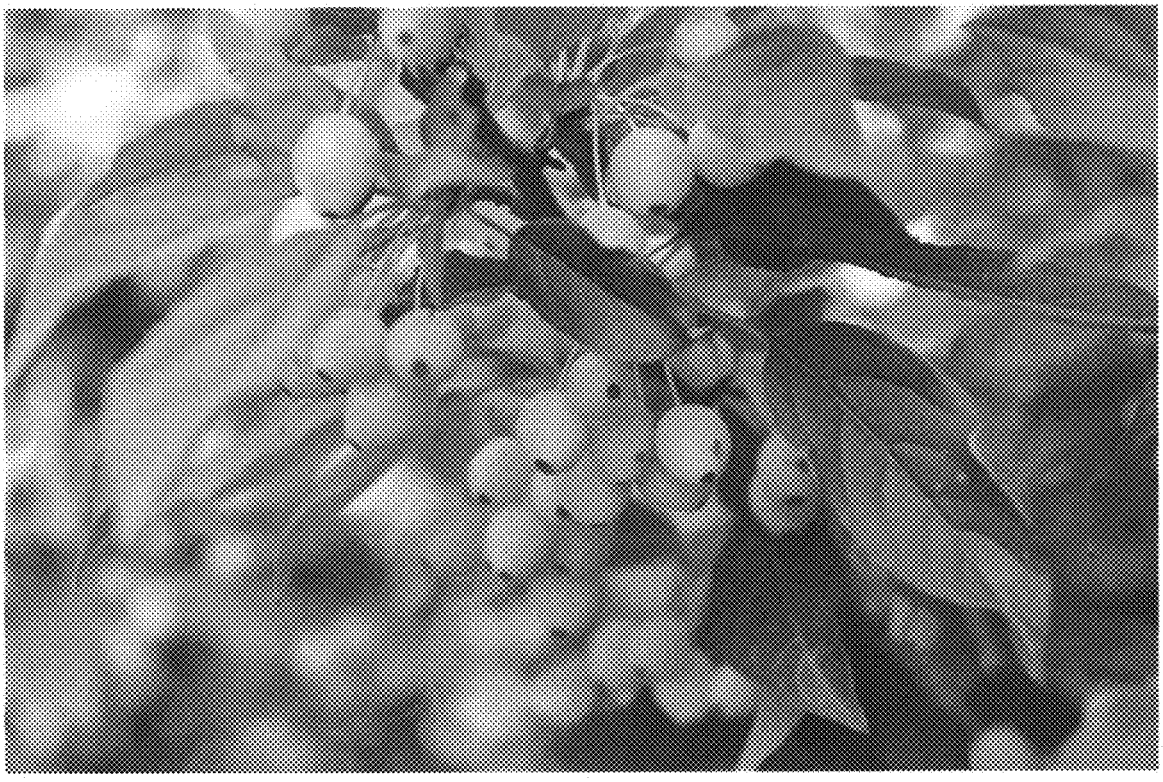
FIG. 6: Shows a close up of the original tree at 10 years of age with fruit
Figure 7:
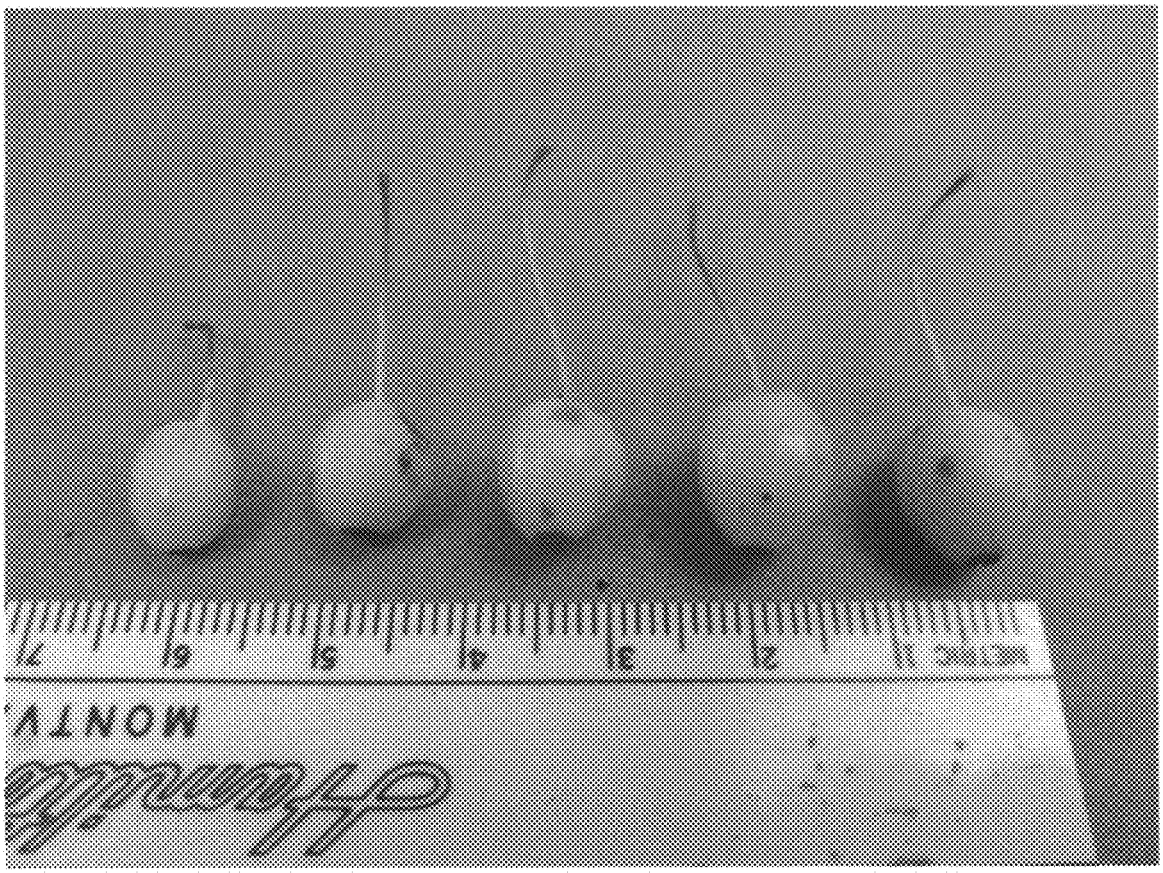
FIG. 7: Shows a close-up of fruit on a display board with a scale.
Figure 8:
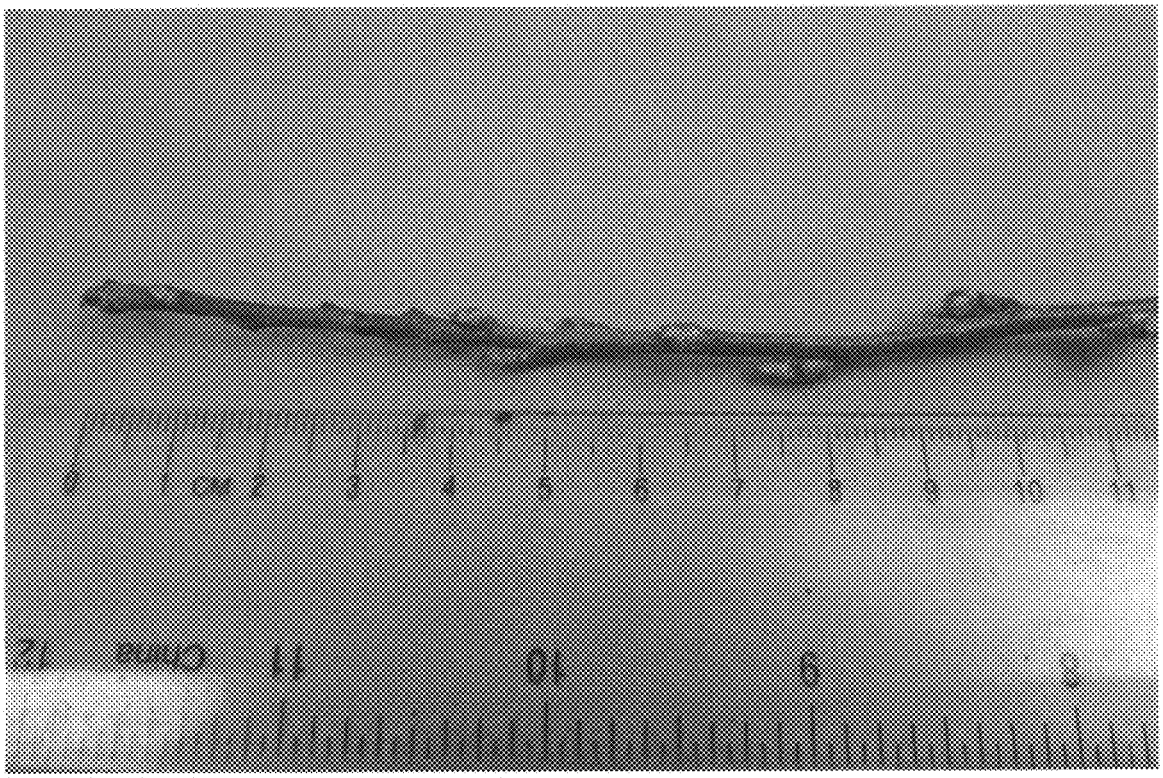
FIG. 8: Shows a dormant branch tip with emerging buds.
Figure 9:
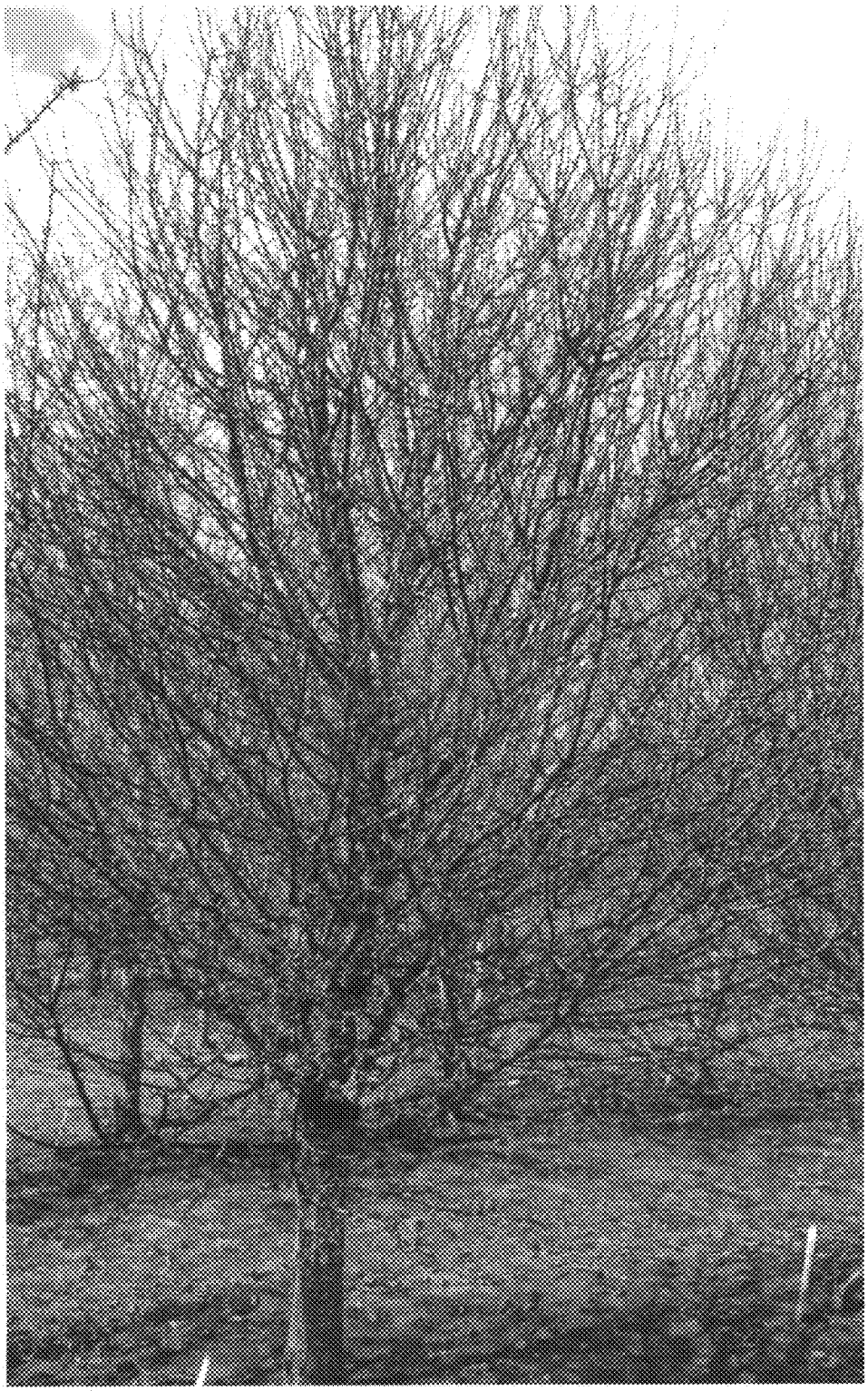
FIG. 9: Shows a tree at 10 years of age without foliage just before bud break.

The following detailed description of the 'JFS KW218MX' variety is based on observations of the original tree growing in Boring, Oreg. and of two and three year old asexually reproduced progeny. The observed progeny were trees which were growing in Canby, Oreg. Color descriptions are made with reference to The Royal Horticultural Society (London) Colour Chart 1986, except where ordinary dictionary significance of color is indicated.

Scientific name: *Malus* 'JFS KW218MX'.

Parentage:

*Seed parent*.—Open pollinated seedling of *Malus* 'KW-83MX'.

*Pollen parent*.—Unknown.

Tree:

*Overall shape*.—Upright Pyramidal.

*Height*.—*At* 12 years of age, about 4.5 meters high.

*Width*.—At 12 years of age 2 meters spread.

*Caliper* (*trunk diameter*).—At 12 years of age, about 130 mm at 100 mm height, 118 mm at 1 m height.

*Trunk*.—Strong and straight under nursery growing conditions.

*Trunk bark texture*.—Smooth, vertical fissures with age.

*Trunk bark color*.—Greyed Green 197B to 197C.

*Immature bark color*.—Yellow Green 144A.

*Mature bark color*.—Greyed Orange 166A to 165A.

*Lenticels*.—Elongated to oval 0.5 mm long by 0.25 mm wide. Greyed Orange 165C in color; disappearing after 3 or 4 years.

*Branch color*.—Greyed Brown 199A.

*Branch lenticels*.—Greyed Orange 165C, 0.25 mm to 0.5 mm in length.

*Dormant buds*.—Elongated oval with acute tip, imbricate scales, 2 mm×5 mm.

*Internodes*.—Average internode length is about 15-20 mm on one-year old shoots.

*Hardiness*.—Has tolerated temperatures to 10° F. in Boring, Oreg. which is the lowest temperature experienced at this location. It is believed to have USDA zone 4 cold hardiness similar to other plants of the same species.

*Disease resistance*.—Excellent resistance to fireblight (*Erwinia amylovora*), powdery mildew (*Podosphaera leucotricha*), and apple scab (*Venturia inaequalis*) on foliage and fruit.

Leaves: Except as otherwise noted, observations are from twenty vigorous growth leaves.

*Arrangement*.—Alternate.

*Type*.—Simple, entire.

*Texture*.—Smooth, with slight undulation between the veins on the upper surface of the leaf.

*Sheen*.—Glossy on the upper surface of the leaf.

*Length*.—Averaging 50 mm-70 mm.

*Width*.—Averaging 20 mm to 30 mm.

*Petioles*.—10 mm to 15 mm long, about 1-2 mm in diameter.

*Overall shape*.—Ovate.

*Margin*.—Serrulate.

*Tip*.—Acute.

*Base*.—Acute.

*Lobes*.—Sometimes present.

*Spring leaf color*.—Green 140A.

*Summer leaf color*.—Upper leaf surface: Green 137A to 137C. Lower leaf surface: Green 138B to 138C. Vein: Green 138C.

*Fall leaf color*.—Foliage turns Orange Yellow 19A to Orange Yellow 21A.

*Fall color begins*.—November 1$^{st}$ (Boring, Oreg. 2020).

*Fall color peak*.—November 15$^{th}$ (Boring, Oreg. 2020).

*Fall color ends*.—December 1st (Boring, Oreg. 2020).

*Pubescence*.—None.

*Persistence*.—Tree is deciduous.

Flowers:

*Overall*.—Number of flowers per cluster: 4 to 5 single flowers.

*Shape*.—Symmetrical, rounded, 5 petals, not cupped.

*Size*.—Approximately 28 mm to 32 mm in diameter.

*Flowers buds*.—Buds emerge small & rounded Red-Purple 64B to Red-Purple 64C in color. Buds increase in size to 8-10 mm long by 4-5 mm wide. Before opening they are White 155B blushed Red-Purple 63C on the petal margins.

*Petals*.—Five petals per flower, elongated oval in shape. 7-8 mm wide×15-18 mm long. Color White 155B.

*Petal margins*.—Free relative to their position on the flower.

*Sepals*.—Smooth, Acute, 6 mm in length, 3 mm wide at the base tapering to a point. Green 142A.

*Stamens*.—About 15 to 20 stamens, 8-10 mm long, arranged concentrically around pistil. White 155B.

*Anthers*.—Yellow Orange 22A. 1 to 1.5 mm long by 0.5 mm to 0.25 mm in diameter.

*Pistil*.—Yellow Green 145A Compound, 3 to 5 branched, length 8 mm-10 mm.

*Pollen*.—Abundant, Orange 26A in color.
*Pedicel*.—18 mm to 24 mm long by 0.5 mm to 0.6 mm in diameter. Yellow Green 146B.
*Pubescence*.—Yes on the upper side of the sepal.
*Fragrance*.—Slightly sweet.
*Flowering date*.—In Boring, Oreg. 2020 (An average Bloom Year). First bloom April 6th, peak bloom April 15th, last bloom May 1st.

Fruit: Observations are from a sampling of typical fruit.
*Cluster*.—3 to 5 fruits per cluster.
*Size*.—Typical fruit is 7 mm to 8 mm in diameter by 10 mm to 12 mm long.
*Shape*.—Ovoid, longer than wide.
*Skin*.—Smooth.
*Lenticels*.—None observed.
*Calyx*.—Usually absent, small when present, 2-3 mm in diameter.
*Color*.—Immature summer fruit is Yellow Green 144A ripening to Yellow Orange 17A in October.
*Seeds*.—Typically 2-3 per fruit, ovoid to rounded, 3 mm long and about 2 mm wide with a smooth surface, Greyed Orange 164A to Greyed Orange 164B in color.
*Fruit production*.—Moderate to heavy depending on the year.
*Fruit persistence*.—80% still persistent Nov. 30, 2020.
*Usage*.—Ornamental, non-edible.

COMPARISON TO THE SEED PARENT

Compared to the seed parent tree 'KW-83MX', the claimed cultivar 'JFS KW218MX' has a more defined compact pyramidal shape. The fruit is 7-8 mm in diameter, as compared to 10 mm-12 mm diameter fruit of 'KW-83MX'. The foliage is also of better quality with a glossy sheen as compared to 'KW-83MX'.

COMPARISON TO OTHER SIMILAR VARIETIES

The following table provides a comparison of 'JFS KW218MX' to 'JFS-KW207' (patented; U.S. Plant Pat. No. 27,954) and 'Schmidtcutleaf' (unpatented) varieties.

| | Malus 'JFS KW218MX' | Malus 'JFS-KW207' | Malus 'Schmidtcutleaf' |
|---|---|---|---|
| Form | Upright Pyramidal | Rounded | Upright Vase |
| Leaf | Simple, entire. | Simple, entire, sometimes with lobes | |
| Leaf Length | 50 mm to 70 mm | 70 mm to 80 mm | 90 mm to 120 mm |
| Leaf Width | 20 mm to 30 mm | 30 mm to 40 mm | 50 mm to 60 mm |
| Petiole | 10-15 mm | 20 mm | 25 mm-30 mm |
| Upper Leaf Color | Green 137A to Green 137C | Green 137A to Green 139A | Green 189A to Green 139B |
| Flowers | Single. About 28 mm to 32 mm in diameter. White 155B | Single. About 25 mm to 30 mm in diameter. White 155B | Single. About 28 mm to 32 mm in diameter. White 155B |
| Petals | 7-8 mm wide 15-18 mm long | 8-10 mm wide 14-16 mm long | 6-8 mm wide 18-20 mm long |
| Fruit Color | Yellow Orange 17A | Yellow Orange 21B to Yellow Orange 22A | Yellow Orange 21A to Yellow Orange 23B |
| Fruit Size | 10 to 12 long × 7-8 mm wide | 8 to 10 mm long × 8-11 mm wide | 6 to 8 mm long × 8-10 mm wide |
| Fruit Shape | Ovoid, longer than wide | Round | Round |

I claim:

1. A new and distinct variety of crabapple tree named 'JFS KW218MX', as herein illustrated and described.

* * * * *